United States Patent [19]

Chu et al.

[11] Patent Number: 4,788,374

[45] Date of Patent: Nov. 29, 1988

[54] ZEOLITE CATALYSIS

[75] Inventors: Pochen Chu, West Deptford; William E. Garwood, Haddonfield, both of N.J.; Albert B. Schwartz, Philadelphia, Pa.

[73] Assignee: Mobil Oil Corporation, New York, N.Y.

[21] Appl. No.: 137,223

[22] Filed: Dec. 23, 1987

[51] Int. Cl.$^4$ ................................................ C07C 2/02
[52] U.S. Cl. ..................................... 585/533; 208/46
[58] Field of Search ........................... 585/533; 208/46

[56] References Cited

U.S. PATENT DOCUMENTS 4,203,869  5/1980  Rollmann .............................. 502/69
4,670,614  6/1987  Ushio et al. ........................... 585/533

*Primary Examiner*—Curtis R. Davis
*Attorney, Agent, or Firm*—Alexander J. McKillop; Michael G. Gilman; L. G. Wise

[57] ABSTRACT

A surface-inactive shape selective metallosilicate catalyst, useful for the conversion of lower molecular weight olefins to liquid hydrocarbons such as gasoline, distillate, and high viscosity lube oils, is prepared by a process comprising forming a silica shell on a metallosilicate core by crystallizing silica in the presence of fluoride ion onto the surface of the core.

10 Claims, No Drawings

ZEOLITE CATALYSIS

FIELD OF THE INVENTION

This invention relates to a process for preparing an essentially surface-inactive medium pore shape selective crystalline metallosilicate catalyst. The novel catalyst can be employed in hydrocarbon conversion reactions to prepare more valuable products.

BACKGROUND OF THE INVENTION

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al., as disclosed in European patent application No. 83301391.5, published Sept. 29, 1983. In U.S. Pat. Nos. 4,150,062; 4,211,640 and 4,227,992 Garwood et al disclose the operating conditions for the Mobil Olefin to Gasoline/Distillate (MOGD) process for selective conversion of $C_{3}+$ olefins to mainly aliphatic hydrocarbons.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2-C_8$ alkenes may be converted; however, the distillate mode conditions do not convert a major fraction of ethylene. A typical reactive feedstock consists essentially of $C_3-C_6$ mono-olefins, with varying amounts of nonreactive paraffins and the like being acceptable components.

In the past various methods have been employed for preparing surface-inactive catalysts. Several techniques may be used to increase the relative ratio of intra-crystalline acid sites to surface active sites. This ratio increases with crystal size due to geometric relationship between volume and superficial surface area. Deposition of carbonaceous materials by coke formation can also shift the effective ratio. Enhanced effectiveness is observed where the surface acid sites of small crystal zeolites are reacted with a chemisorbed organic base or the like.

Catalysts of low surface activity can be obtained by using medium pore zeolites of small crystal size that have been selectively deactivated by basic compounds, such as bulky amines and/or phosphines having an effective critical dimension or cross section diameter of about 6-7 Angstrom or greater. Another surface modification technique is deactivation by treating with metal compounds.

The catalysts may be treated with organic silicon compounds, as described in U.S. Pat. Nos. 4,100,215 (Chen) and 4,002,697 (Chen) to impart the desired degree of surface deactivation while being essentially free of carbonaceous deposits. Such treatment involves contacting the catalyst with a silane surface modifying agent capable of deactivating catalytic (acidic) sites located on the external surface of the zeolite by chemisorption.

It is a main object of this invention to provide an improved process for upgrading olefins to valuable lubricant 1 quality product. Significantly improved linearity can be achieved by employing a catalyst comprising a medium pore shape selective siliceous metallosilicate with a substantially inactive surface.

SUMMARY OF THE INVENTION

A process for preparing a unique shape selective porous silica shell catayst has been discovered. The silica shell, essentially free of acid sites surrounds a crystalline medium pore shape selective metallosilicate core containing tetrahedrally coordinated meta acid sites.

In addition, the unique catalyst has proven to be an effective agent for conversion of lower molecular weight olefins to gasoline and/or distillate range hydrocarbons and high viscosity lube oils.

These and other objects and features of the invention will be understood from the following detailed description.

DETAILED DESCRIPTION OF THE INVENTION

In this description, metric units and parts by weight are employed unless otherwise stated. The catalyst prepared according to the process of the present invention comprises an inner portion and an outer portion disposed as a porous shell around the inner portion wherein the inner portion comprises a medium pore metallosilicate and the outer portion comprises crystalline silica substantially free of acid sites, the outer portion being crystallized from an alkaline silicate solution containing fluoride ion.

The inner portion which defines the interior of the catlyst is a crystalline metallosilicate material which can be selected from the group consisting of aluminosilicates, gallosilicates, ferrosilicates, borosilicates and mixtures thereof. This inner portion is a medium pore crystalline metallosilicate with a silica:metal oxide molar ratio of about 10:1 to about 300:1. The pore size of the core material is about 5 to 7 angstroms. The average crystal size of the metallosilicate material is about 0.02 to about 5.0 microns. The acid cracking activity ($\alpha$-value) of the metallosilicate is at least about 40.

Developments in zeolite technology have provided a group of medium pore siliceous materials having similar pore geometry. Most prominent among these intermediate pore size zeolites is ZSM-5, which is usually synthesized with acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The metallosilicate catalysts useful in the process of this invention include siliceous zeolites generally known as medium pore, shape-selective catalysts. Recent developments in zeolite technology have provided a group of medium pore siliceous materials having similar pore geometry. Most prominent among these intermediate pore size zeolites is ZSM-5, which is usually synthesized with active acid sites by incorporating a tetrahedrally coordinated metal, such as Al, Ga, B, or Fe, within the zeolitic framework. While suitable zeolites having a coordinated metal oxide to silica molar ratio of 20:1 to 200:1 or higher may be used, it is advantageous to employ a standard aluminosilicate ZSM-5 having a silica:alumina molar ratio of about 25:1 to 70:1, suitably modified to provide an inactive surface. The members of the class of zeolites useful for such catalysts have an effective pore size of generally from about 5 to about 8 Angstroms such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually have pores of large size, e.g. greater than 8 Angstroms. The method by which Constraint Index is determined is described fully in U.S. Pat. No. 4,016,218, (Haag et al) incorporated herein by reference for details of the method. It is noted that the Constraint Index is determined with the hydrogen form of the zeolite, but that the property is believed to be an atttribute of the crystal structure.

Constraint Index (CI) values for some typical materials are shown in Table 1.

TABLE 1

| Zeolite | CI | (at test temperature) |
| --- | --- | --- |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| Zeolite Beta | 0.6–2.0 | (316° C.–399° C.) |

The above-described Constraint Index is an important and even critical definition of those ZSM-5 type zeolites which are useful in the instant invention. Zeolites having a CI of about 1 to 12 are preferred. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

The class of highly siliceous zeolites defined herein is exemplified by ZSM-5, ZSM-11, ZSM-12, ZSM-22, ZSM-23, ZSM-35, ZSM-48, and other similar materials. ZSM-5 is described in U.S. Pat. No. 3,702,886 (Argauer et al); ZSM-11 in U.S. Pat. No. 3,709,979 (Chu); ZSM-12 in U.S. Pat. No. 3,832,449 (Rosinski et al); ZSM-22 in U.S. Pat. No. 4,046,859 (Plank et al); ZSM-23 in U.S. Pat. No. 4,076,842 (Plank et al); ZSM-35 in U.S. Pat. No. 4,016,245 (Plank et al); and ZSM-48 in U.S. Pat. No. 4,397,827 (Chu); incorporated herein by reference. Similar layered zeolites are disclosed in U.S. Pat. No. 4,088,605 (Rollman). In a preferred example the catalyst of the present invention comprises aluminosilicate H-ZSM-5 zeolite free of hydrogenation-dehydrogenation components.

It is desirable in this invention to employ variants of the zeolite that have at least a moderate amount of acid activity. A zeolite having a lower silica-to-alumina ratio (e.g. 10:1 to 100:1) is usually preferred since the acid cracking activity as measured by alpha value of the former is higher, typically about 100 to 500. The alpha test, which provides a measure of the relative rate constant of the zeolite for cracking normal hexane (i.e. the alpha value), is described by Miale et al. in Journal of Catalysis, Volume 6, No. 2, Oct., 1966, and is herein incorporated by reference as if fully set forth.

The zeolite component of the catalyst may be the sole component, i.e. it may be shaped into pellets using known methods, and in such shaped form it can serve as an effective catalyst in the process of this invention. The zeolite may be composited with a binder, such as for example with alumina, to form catalyst particles by extrusion or other methods known in the art. Extrudate particles containing about 65 wt. % zeolite and 35 wt. % alumina binder exemplify a catalyst suitable for use in the process of the present invention.

The outer portion of the catalyst is a crystalline silica material disposed as a porous shell around the core or inner portion. The silica shell, crystallized from an alkaline silicate solution containing fluoride ion, is substantially free of acid sites such as tetrahedrally coordinated metal oxides, for example, aluminum oxide, gallium oxide, iron (II) or iron (III) oxide, and boron oxide. Although not wishing to be bound by theory, it is believed that the crystalline silica shell outer portion of the catalyst may contain a substantial amount of fluoride-silicon bonds in place of hydroxide-silicon bonds. At any account, the crystalline silica shell outer portion contains a substantial amount of fluoride. This feature further reduces the acid activity of the porous outer shell. The amount of fluoride incorporated within the outer portion of the catalyst is typically in the range of about 0.01 to 1% by weight based on total crystal weight, preferably about 0.05 to 0.5% by weight.

The outer portion of the catalyst is in the range of about 10 to 50% by weight of the total product, preferably about 20 to 30% by weight.

A process for preparing the catalyst, which is a siliceous zeolite particle, is a series of steps comprising preparing an aqueous alkaline solution comprising a source of silicate ions, optionally an organic directing agent, and a source of hydroxide ions; mixing the aqueous solution with an aqueous dispersion of crystalline metallosilicate to form a homogenous mixture which is subsequently heated; and adding an aqueous solution of a fluoride compound to the homogeneous mixture and heating the resulting composition at a temperature to effectively form a particle comprising a crystalline silica outer shell substantially free of acid sites on a metallosilicate core. The particle is withdrawn from the composition and treated by a series of washing, drying and calcining steps to yield an active catalyst having internal acid sites.

The aqueous alkaline silica solution is prepared by mixing an alkali metal or alkaline earth metal base such as sodium hydroxide, optionally an organic directing agent such as tetrapropylammonium bromide, and a source of silicate ions such as colloidal silica (Ludox LS, 30% silica). The organic directing agent serves to promote the contact between reactive species.

Other suitable organic directing agents are disclosed in U.S. Pat. Nos. 4,139,600 and 4,151,189, incorporated by reference.

An alternative process for preparing the catalyst comprises reacting a source of metal oxide and a source of silica under crystallization conditions to obtain an intermediate metallosilicate product which is about 50% to 75% crystallized, adding a source of fluoride ions, and completing the crystallization procedure with heating.

The source of silicate ions can be the oxide, silicic acid, or salts of the acid such as sodium silicate. There must be present in the reaction mixture an amount of silicate ions to effectively form a porous shell covering the metallosilicate core.

The aqueous solution containing the fluoride compound is prepared by mixing a compound which generates fluoride ions in situ with water. The compound is present in an amount sufficient to complex any dissolved aluminum ion. In a preferred embodiment, the fluoride compound is ammonium fluoride. When a gaseous species such as hydrogen fluoride or fluorine gas is employed, the reactive fluoride compound can be injected directly into the previously prepared homogeneous mixture containing a source of silicate ions and metallosilicate particles by known methods such as bubbling the gas through the mixture.

The effective temperature for forming the crystalline silica outer shell is about 80° C. to 200° C., preferably about 100° C. The reaction is conducted in an autoclave at autogenous or higher pressures.

The process dramatically increases the relative ratio of intra-crystalline acid sites to surface active sites. Acid activity on the surface of a porous crystalline acidic zeolite catalyst having a silica:alumina molar ratio greater than about 10 is reduced by a novel method. A method comprises contacting the acidic zeolite catalyst with a hot alkaline solution comprising silicate ions, an organic directing agent, and a source of hydroxide ions to form a homogenous colloidal suspension; adding a source of fluoride ions to the suspension to form a chemically reactive aqueous composition; and heating the composition at a temperature to effectively deposit an outer porous shell comprising silicaon the acid zeolite catalyst, thereby reducing the acid activity on the surface of the catalyst. The acidic zeolite catalyst having a deposited porous outer shell comprising silica and fluoride is separated from the chemically reactive aqueous composition, washed, dried and calcined to form a zeolite catalyst having internal acid sites and a substantially acid-free surface.

Shape-selective oligomerization, as it applies to the conversion of $C_2$–$C_{10}$ olefins over ZSM-5, is known to produce higher olefins up to $C_{30}$ and higher. As reported by Garwood in Intrazeolite Chemistry 23, (Amer. Chem. Soc., 1983), reaction conditions favoring higher molecular weight product are low temperature (200°–260° C.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for propylene is set forth for purposes of explanation, and it should be taken as a theoretical path, as the process is presently understood by workers in the field.

$C_3^=$ (propylene) oligomerization
$C_6^=$, $C_9^=$, $C_{12}^=$, etc.
($C_3$ oligomers)

Isomerization and cracking
$C_3^=$, $C_4^=$, $C_5^=$, $C_6^=$, $C_7^=$, etc.;

Interpolymerization

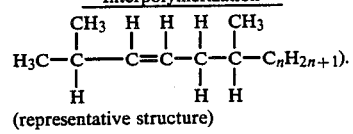

(representative structure)

The desired oligomerization-polymerization products include $C_{10}{}^+$ substantially linear aliphatic hydrocarbons. The ZSM-5 catalytic path for propylene feed provides a long chain with approximately one lower alkyl (e.g., methyl) substituent per 8 or more carbon atoms in the straight chain. The lubricant range final product can be depicted as a typical linear molecule having a sparingly-substituted (saturated) long carbon chain.

The final molecular conformation is influenced by the pore structure of the catalyst. For the higher carbon numbers, the structure is primarily a methyl-branched straight olefinic chain, with the maximum cross section of the chain limited by the 5.4×5.6 Angstrom dimension of the largest ZSM-5 pore. Although emphasis is placed on the normal 1-alkenes as feed stocks, other lower olefins such as 2-butene or isobutylene, are readily employed as starting materials due to rapid isomerization over the acidic zeolite catalyst. At conditions chosen to maximize heavy distillate and lubricant range products ($C_{20}{}^+$) the raw aliphatic product is essentially mono-olefinic. Overall branching is not extensive, with most branches being methyl at about one branch per eight or more atoms.

The catalyst of the present invention is particularly suited for olefin oligomerization reactions wherein highly branched oligomers are to be avoided in the product effluent. As stated above, the olefin conversion reactions taking place at the acid sites inside the channels or pores of the catalyst particles produce essentially linear aliphatic hydrocarbons with a minimum amount of branching. Since there are practically no acid sites on the outer surface of the treated catalyst, polymerization and isomerization reactions are essentially eliminated and highly branched hydrocarbons are not generated as molecular rearrangement products.

The catalyst particles prepared according to the present method can be employed in a process for oligomerizing lower molecular weight olefins comprising contacting a feed comprising a $C_2$–$C_{20}$ olefin or mixtures thereof under reaction conditions in an oligomerization reaction zone with a catalyst comprising an inner portion and an outer portion disposed as a shell around the inner portion, wherein the inner portion comprises a medium pore shape-selective acidic crystalline metallosilicate and the outer portion comprises a metal-free crystalline silica, to produce hydrocarbons boiling in the gasoline and/or distillate range. The hydrocarbons boiling in the gasoline and/or distillate range are withdrawn from the reaction zone, separated, and recovered as products.

A process for producing hydrocarbons boiling in the gasoline and/or distillate range from lower molecular weight olefins under conditions of elevated temperature and pressure with a shape selective medium pore crystalline aluminosilicate catalyst is improved by reducing the non-shape selective surface-cracking and/or surface isomerization activity of the aluminosilicate catalyst. This reduction of surface activity is achieved by preparing an aqueous solution comprising colloidal silica, an organic directing agent, and a source of hydroxide ions; mixing the aqueous solution with an aqueous dispersion of shape-selective medium pore crystalline aluminosilicate to form a homogenous mixture which is subsequently heated; adding an aqueous solution comprising a source of fluoride ions to the homogeneous mixture to form a reactive composition; and heating the reactive composition at a temperature to effectively form a surface-inactive catalyst comprising a crystalline fluoride-containing silica outer shell on an aluminosilicate. The surface-inactive catalyst is separated from the reactive composition for washing, drying, and calcining of the catalyst; and removed to the reaction zone for contact with the olefin feedstock.

In a similar fashion a high viscosity index lube oil is prepared from a feedstock comprising lower molecular weight olefins by a process comprising contacting the feedstock at reaction conditions in a reaction zone with a catalyst comprising an inner portion and an outer portion disposed as a porous shell around the inner portion, the inner portion comprising a medium pore shape-selective crystalline acidic aluminosilicate, and the outer portion comprising a fluoride-containing crystalline silica shell; and withdrawing from the reaction zone a hydrocarbon liquid comprising a high viscosity index lube oil and higher boiling hydrocarbons. The lube oil is separated and recovered as product boiling above about 340° C. The product lube oil has a viscosity index of at least about 110. Production of lube oil with a conventional HZSM-5 catalyst yields a lubricant oil bottoms fraction having a viscosity index of about 70. This is because the bottoms fraction contains a substantial amount of highly branched hydrocarbon material. The viscosity index of a hydrocarbon lube oil is related to its molecular conformation. Extensive branching in a molecule usually results in a low viscosity index.

The surface-inactive metallosilicate catalyst of the present invention can be employed in a variety of acid-catalyzed hydrocarbon conversion processes that depend upon a shape-selective catalyst. Such conversion processes include aromatics alkylation, xylenes isomerization, selective hydrocracking, dewaxing, aliphatics (e.g., olefin) isomerization and the like.

EXAMPLE 1

A surface-inactive small crystal acid ZSM-5 zeolite is prepared as follows. Preparation of a first solution is conducted by adding sequentially 12 g. of sodium hydroxide, 30 g. of tetrapropylammonium bromide, and 383 g. of colloidal silica (Ludox LS, 30% silica) to 200 g. of water. A second solution is prepared by dispersing 115 g. of small crystal (0.02–0.05 micron) acid ZSM-5 having a silica:alumina molar ratio of 40 in 300 g. of water.

The first solution is added to the second solution and blended into a homogeneous mixture. The mixture is charged to an autoclave and heated at 99° C. for a period of 3 hours with stirring. Then a third solution containing 23 g. of ammonium fluoride in 50 g. of water is added to the autoclave which is heated for another 16 hours. The solid product is then collected on a filter, washed with water, and dried in air. The product is precalcined in an inert nitrogen atmosphere, cation exchanged with ammonium nitrate, and finally calcined in air.

EXAMPLE 2

Propylene is converted to liquid hydrocarbons at oligomerization conditions over a surface-deactivated catalyst as follows. A catalyst prepared according to Example 1 is sized to about 14–25 mesh. About 5 g. of the catalyst is placed in a stainless steel reactor having an inside diameter of ⅜ inch. The reactor is purged with hydrogen at 482° C. and at atmospheric pressure for one hour.

Propylene is then directed over the catalyst at a weight hourly space velocity (WHSV) of 0.5, an average temperature of 211° C., and a pressure of 10,300 kPa for a period of 24 hours. The liquid recovery after 24 hours is 78% by weight.

The temperature is then raised to 234° C. and propylene is directed over the catalyst for a period of 36 hours. The liquid recovery is 99% by weight.

Again the temperature is raised, this time to 261° C. A stream of propylene is passed over the catalyst for 24 hours to give a liquid recovery of 90% by weight.

A mixture of the liquid products is distilled to achieve a bottoms lube fraction of 13% by weight (based on propylene feed). The lube oil fraction has the following properties:

Gravity (API): 41.6
Gravity (Specific): 0.8174
Pour point (°C.): −18
KV @40° C., : cs 7.56
KV @100° C., cs: 2.27
Viscosity Index: 111.9

EXAMPLE 3

As a comparative experiment, a conventional crystalline acidic ZSM-5 catalyst having a silica:alumina molar ratio of 70:1 is employed for the conversion of propylene. The catalyst is sized to 14-25 mesh and an amount of about 5 g. is placed in a stainless steel reactor having an inside diameter of ⅜ inch. The reactor is purged with hydrogen at 482° C. and at atmospheric pressure for one hour.

Propylene is then directed over the catalyst at a weight hourly space velocity (WHSV) of 0.5, an average temperature of 205° C., and a pressure of 10,300 kPa for a period of 48 hours. The liquid recovery after 48 hours is 98% by weight.

The temperature is then raised to 238° C. and propylene is directed over the catalyst for 24 hours to give a liquid recovery of 97% by weight. A mixture of the liquid products is distilled to achieve a bottoms lube fraction of 10% by weight (based on propylene feed). The lube oil fraction has the following properties:

Gravity (API): 33.3
Gravity (Specific): 0.8587
Pour Point (°C.): −34
KV @40° C., cs: 56.35
KV @100° C., cs: 6.93
Viscosity Index: 70

EXAMPLE 4

A test to measure the surface activity of the prepared catalysts was devised. A feed of 1,3,5-Triethylbenzene (TEB) is passed over a catalyst sample at a liquid hourly space velocity (LHSV) of 20 and at a temperature of 260° C. A molecule of 1,3,5-TEB is too bulky to enter the internal pores of a zeolite having a Constraint Index of 1-12. Therefore the equilibrium conversion reaction of 1,3,5-TEB can occur only at the acid sites on the surface of such medium pore zeolites. The results of the test are as follows:

| Method of ZSM-5 preparation | $SiO_2Al_2O_3$ (bulk) | % TEB converted |
| --- | --- | --- |
| Conventional | 70 | 77 |
| Example 1 | 64 | 6 |

The results of this test confirm the fact that a catalyst prepared according to the presently disclosed process has low surface activity

EXAMPLE 5

A caustic solution is prepared by dissolving 1.1 parts of aluminum sulfate, 2.54 parts of 50% NaOH and 9.45 parts of pyrrolidine in 171 parts of de-ionized water. One part of ZSM-23 (100% solid basis) and 28.8 parts of Hi Sil 233 are then added to form a thick slurry. The crystallization is carried out at 320° F. and 80 rpm agitation. The crystallization is complete in about 20 hours. The filtered, water-washed and dried solid product is found to be pure ZSM-23 by X-ray diffraction method. The crystals are needle shaped, having average crystallite length about 0.5 micron and average diameter of about 0.05 micron.

EXAMPLE 6

Surface-inactivate crystals having the structure of ZSM-23 are prepared as follows. A caustic solution is prepared by dissolving 0.51 g of NaOH and 11.7 g of pyrrolidine in 156 g of water. To this solution 83 g of Ludox AS-40, 3 g of NH₄F and ZSM-23 (product from Example 5) seed slurry (33 g seed in 60 g of water) are added sequentially to form a silica gel. The mixture is heated at 150° C. in an autoclave for about 46 hours. The solids are filtered, water washed, dried and found to have the structure of ZSM-23 by X-ray diffraction method. The sample contains 0.24% of fluorine and 0.65% of sodium. The sample is then converted to acid form by precalcination in nitrogen at 537° C., ammonium exchange to remove sodium and activation in air at 537° C. for 3 hours. The final product contains 0.02% residual sodium.

EXAMPLE 7

The surface-inactivate ZSM-23 sample prepared in Example 5 is tested by the TEB test described in Example 4. The results are as follows:

| Method of ZSM-23 preparation | $SiO_2/Al_2O_3$ (bulk) | % Conv. of TEB |
| --- | --- | --- |
| No Silica Shell (Exam. 5) | 120 | 11 |
| With Silica Shell (Exam. 6) | 130 | 0.8 |

The results confirm the fact that the ZSM-23 prepared by the method in Example 6 has low surface activity.

While the invention has been described by reference to certain embodiments, there is no intent to limit the inventive concept except as set forth in the following claims.

We claim:

1. A process for preparing hydrocarbons boiling in the gasoline and/or distillate range by contacting a feedstock comprising lower molecular weight olefins in a reaction zone under conditions of elevated temperature and pressure with a shape selective crystalline aluminosilicate catalyst, comprising:
   reducing the non-shape selective surface-cracking and/or surface isomerization activity of the aluminosilicate catalyst by a process comprising:
   preparing an aqueous solution comprising colloidal silica, optionally an organic directing agent, and a source of hydroxide ions;
   mixing the aqueous solution with an aqueous dispersion of shape-selective crystalline aluminosilicate to form a homogeneous mixture which is subsequently heated;
   adding an aqueous solution comprising a source of fluoride ions to the homogeneous mixture to form a reactive composition;
   heating the reactive composition at a temperature to effectively form a surface-deactivated catalyst comprising a crystalline fluoride-containing silica outer shell on an aluminosilicate;
   withdrawing the surface-deactivated catalyst from the reactive composition for washing, drying, and calcining of the catalyst; and
   removing the catalyst to the reaction zone for contact with the olefin feedstock.

2. A process according to claim 1 wherein the crystalline aluminosilicate catalyst comprises medium pore zeolite.

3. A process according to claim 2 wherein the medium pore aluminosilicate catalyst comprises ZSM-5.

4. A process for preparing a high viscosity index lube oil from a feedstock comprising lower molecular weight olefins comprising:

contacting the feedstock at reaction conditions in a reaction zone with a catalyst comprising an inner portion and an outer portion disposed as a porous shell around the inner portion, the inner portion comprising a medium pore shape-selective crystalline acidic metallosilicate, and the outer portion comprising a fluoride-containing crystalline silica shell substantially free of acid sites; and withdrawing from the reaction zone a hydrocarbon liquid comprising a high viscosity index lube oil and higher boiling hydrocarbons.

5. A process according to claim 4 wherein the lube oil is separated and recovered as product boiling above about 340° C.

6. A process according to claim 5 wherein the product lube oil has a viscosity index of at least about 110.

7. The process according to claim 4 wherein the catalyst inner portion consists essentially of aluminosilicate zeolite having the structure of ZSM-5.

8. The process according to claim 4 wherein the catalyst inner portion consists essentially of aluminosilicate zeolite having the structure of ZSM-23.

9. A process according to claim 7 or 8 wherein the porous shell has substantially the same crystalline structure as the inner portion.

10. A process for the shape-selective conversion of hydrocarbons comprising;

contacting the hydrocarbons at reaction conditions with a catalyst comprising an inner portion and an outer portion disposed as a porous shell around the inner portion, the inner portion comprising a shape-selective tetrahedrally coordinated crystalline acidic metallosilicate, and the outer portion comprising a fluoride-containing crystalline silica shell substantially free of acid sites.

* * * * *